United States Patent
Thakur et al.

(10) Patent No.: US 11,684,272 B2
(45) Date of Patent: Jun. 27, 2023

(54) AMBULATORY VASOACTIVITY MONITOR

(71) Applicant: Cardiac Pacemakers, Inc., St. Paul, MN (US)

(72) Inventors: Pramodsingh Hirasingh Thakur, Woodbury, MN (US); Viktoria A. Averina, Shoreview, MN (US); Qi An, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 800 days.

(21) Appl. No.: 16/515,783

(22) Filed: Jul. 18, 2019

(65) Prior Publication Data

US 2020/0037888 A1 Feb. 6, 2020

Related U.S. Application Data

(60) Provisional application No. 62/714,417, filed on Aug. 3, 2018.

(51) Int. Cl.
*A61B 5/00* (2006.01)
*A61B 5/021* (2006.01)
(Continued)

(52) U.S. Cl.
CPC ............ *A61B 5/021* (2013.01); *A61B 5/0205* (2013.01); *A61B 5/113* (2013.01); *A61B 5/1116* (2013.01);
(Continued)

(58) Field of Classification Search
CPC ..... A61B 5/021; A61B 5/0205; A61B 5/1116; A61B 5/113; A61B 5/686; A61B 5/7275; A61B 5/0031; A61B 5/02007; A61B 5/024; A61B 5/0285; A61B 5/053; A61B 5/0816; A61B 5/316; A61B 5/349; A61B 5/4035; A61B 7/005; A61B 5/4839; A61N 1/3904; A61N 1/3627; A61N 1/36514; A61N 1/36585; A61N 1/3702; A61N 1/3956
See application file for complete search history.

(56) References Cited

U.S. PATENT DOCUMENTS

| | | | |
|---|---|---|---|
| 8,676,326 B1* | 3/2014 | Farazi | A61N 1/368 607/9 |
| 2008/0132972 A1 | 6/2008 | Shuros et al. | |
| 2018/0325466 A1* | 11/2018 | An | A61B 7/04 |

OTHER PUBLICATIONS

Hallén, Katarina, et al., "Transcutaneous Electrical Nerve Stimulation Induces Vasodilation in Healthy Controls but Not in Refractory Angina Patients", Journal of Pain and Symptom Management, vol. 40 No. 1, Jul. 2010, 95-101.

* cited by examiner

*Primary Examiner* — Rex R Holmes
(74) *Attorney, Agent, or Firm* — Schwegman Lundberg & Woessner, P.A.

(57) ABSTRACT

Systems and methods for monitoring patient vasoactivity are discussed. An exemplary patient monitor system includes a sensor circuit configured to generate a heart sound (HS) metric using a HS signal sensed from a patient, and a vasoactivity monitor configured to monitor vasoactivity, such as degree of vasoconstriction or vasodilation, using the HS metric. The system can provide the monitored vasoactivity to a user to alert patient hemodynamic responses to vasoactive drugs, or initiate or adjust a vasoactive therapy according to the vasoactivity. The system may use the monitored vasoactivity to detect a medical condition such as worsening heart failure, pulmonary edema, or syncope.

20 Claims, 6 Drawing Sheets

(51) Int. Cl.
*A61B 5/0205* (2006.01)
*A61B 5/113* (2006.01)
*A61N 1/39* (2006.01)
*A61B 5/11* (2006.01)
A61B 5/053 (2021.01)
A61N 1/365 (2006.01)
A61B 5/0285 (2006.01)
A61B 5/02 (2006.01)
A61B 5/08 (2006.01)
A61B 5/024 (2006.01)
A61N 1/37 (2006.01)
A61N 1/362 (2006.01)
A61B 5/316 (2021.01)
A61B 5/349 (2021.01)

(52) U.S. Cl.
CPC ............ *A61B 5/686* (2013.01); *A61B 5/7275* (2013.01); *A61N 1/3904* (2017.08); A61B 5/0031 (2013.01); A61B 5/024 (2013.01); A61B 5/02007 (2013.01); A61B 5/0285 (2013.01); A61B 5/053 (2013.01); A61B 5/0816 (2013.01); A61B 5/316 (2021.01); A61B 5/349 (2021.01); A61B 5/4035 (2013.01); A61N 1/3627 (2013.01); A61N 1/36514 (2013.01); A61N 1/36585 (2013.01); A61N 1/3702 (2013.01)

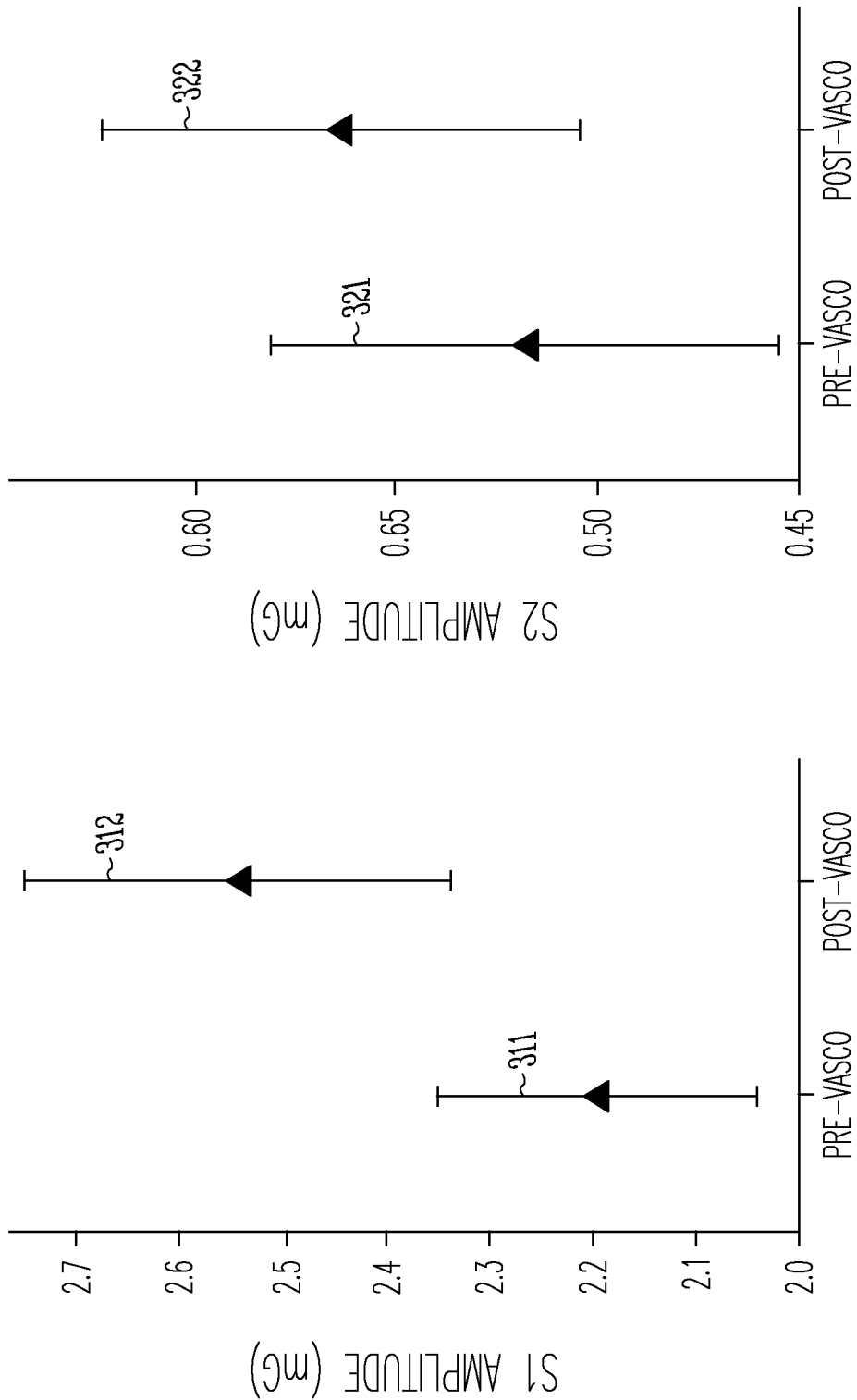

AMBULATORY VASOACTIVITY MONITOR

CLAIM OF PRIORITY

This application claims the benefit of priority under 35 U.S.C. § 119(e) of U.S. Provisional Patent Application Ser. No. 62/714,417, filed on Aug. 3, 2018, which is herein incorporated by reference in its entirety.

TECHNICAL FIELD

This document relates generally to medical devices, and more particularly, to systems, devices and methods for ambulatory monitoring of vasoactivity in a patient.

BACKGROUND

Vasoactivity, or vascular activity, refers to constriction (vasoconstriction) or dilation (vasodilation) of the blood vessels. A vasoactive agent (e.g., a pharmaceutical drug) may modulate vasoactivity by adjusting vascular compliance and/or vascular resistance, which helps the body's homeostatic mechanisms to keep hemodynamics under control. Vasoactive drug therapy is typically used during constant monitoring of patient blood pressure and heart rate.

Vasodilators are vasoactive drugs that help widen blood vessels. They affect the muscles in the walls of arteries and veins, preventing the muscles from tightening and the walls from narrowing. Vasodilators can dilate various blood vessels. For example, dilation of coronary arteries can improve blood flow in myocardium, dilation of leg veins can lower venous return to the heart and thereby limiting the fluid buildup in the lungs, and dilation of the pulmonary arteries and systemic arteries can help relieve the workload of the heart while maintaining adequate systemic circulation. Vasodilators are often combined with other medicines to treat a variety of conditions, including high blood pressure and heart failure (HF). When the blood vessels are widened (or dilated), it is easier for the heart to pump blood, such that the heart burden can be relieved, and the symptoms associated with HF can be improved.

Vasoactive drugs may be administered using a volumetric drug delivery device, such as an intravenous (IV) infusion pump. Dosage of a vasoactive drug may be titrated to achieve a desired hemodynamic outcome. Some vasoactive drugs may have side effects. For vasodilators, typical side effects include tachycardia, heart palpitation, edema, nausea and vomiting, headache, or chest pain. Close monitoring of the patient and dosage control may help prevent or reduce side effects and improve patient outcome.

OVERVIEW

Vasodilator is an important therapeutic agent in treating HF. It is typically used in conjunction with diuretics in patients presenting with increased left-ventricular (LV) filling pressure and high or normal blood pressure. Hemodynamic effects of vasodilators in HF patients can be achieved through Frank-Starling mechanism, which describes a physiologic relationship between the preload (which can be measured as LV end-diastolic volume or pressure) and cardiac output (which can be measured as stroke volume). In HF, the Frank-Starling curve is moved down (flattened) so that more venous return and filling pressure is required to maintain contractility and stroke volume. As a result, increased fluid retention occurs as cardiac dysfunction worsens in I-IF Diuretics, vasodilators, and positive inotropes can improve cardiac performance by reducing preload and intravascular pressure. For example, diuretics may cause fluid loss, thereby shifting the Frank-Starling curve to the left. This intervention alleviates signs of congestion without markedly affecting overall cardiac performance. Positive inotropes improve the contractility of the heart and shift the Frank-Starling curve upward, resulting in improved cardiac output even as preload is reduced. Vasodilators act to either reduce afterload (arterial vasodilators) or preload (venous vasodilators). Arterial vasodilators improve cardiac performance by shifting the curve upward, whereas venous vasodilators reduce preload through an increase the capacitance of the venous system and shift the curve leftward, similar to diuretics. Mixed vasodilators (e.g., ACE inhibitors) result in a combination of both upward and leftward adjustment.

Close hemodynamic monitoring is critical in vasodilator treatment to ensure adequate therapeutic effect with minimal side effects. Conventionally, invasive hemodynamic monitoring is used to monitor cardiac output, strove volume, or LV end-diastolic volume or pressure. Such measurements are suitable for in-clinic patient monitoring of sedentary patients. For ambulatory HF patients receiving vasodilator or diuretic treatment such as in their homes, ambulatory vasoactivity monitoring is generally desired. This may require timely assessment of vasodilation (e.g., in response to vasodilator therapy) and dosage titration if needed. For these reasons, the present inventors have recognized that there remains a need for improved systems, devices, and methods for ambulatory vasoactivity monitoring, such as to assess hemodynamic responses to vasodilator therapy in HF patients.

This document discusses, among other things, systems, devices, and methods for monitoring vasoactivity in a patient. An exemplary patient monitor system may include a sensor circuit configured to generate a heart sound (HS) metric using a HS signal sensed from a patient, and a vasoactivity monitor configured to monitor vasoactivity, such as degree of vasoconstriction or vasodilation, using the HS metric. The monitored vasoactivity may be provided to a user (e.g., a clinician) to alert patient hemodynamic response to, and thus the effects of, vasoactive drugs. The system may include a therapy unit configured to generate or adjust a vasoactive therapy according to the monitored vasoactivity. In some examples, the system may use the monitored vasoactivity to detect a medical condition, such as worsening heart failure (WHF), pulmonary edema, or syncope.

Example 1 is a system for ambulatory monitoring of vasoactivity in a patient. The system comprises a sensor circuit configured to generate a heart sound (HS) metric using a HS signal sensed from the patient, and a control circuit, including a vasoactivity monitor configured to monitor vasoactivity using the generated HS metric and to determine a degree of vasodilation or a degree of vasoconstriction.

In Example 2, the subject matter of Example 1 optionally includes the vasoactivity monitor configured to monitor vasoactivity in response to a vasodilator or vasoconstrictor therapy, and to generate a therapy efficacy indicator using the monitored vasoactivity.

In Example 3, the subject matter of any one or more of Examples 1-2 optionally includes a therapy unit configured to generate or adjust a vasoactive therapy according to the monitored vasoactivity.

In Example 4, the subject matter of Example 3 optionally includes the therapy unit that may include a drug delivery unit configured to controllably administer or adjust a vasodilator agent or a vasoconstrictor agent based on the vasoactivity.

In Example 5, the subject matter of Example 3 optionally includes the therapy unit that may include an electrostimulation circuit configured to initiate or adjust an electrostimulation therapy based on the monitored vasoactivity.

In Example 6, the subject matter of any one or more of Examples 1-5 optionally includes the sensor circuit configured to generate a HS metric using one or more HS components including first (S1), second (S2), third (S3), or fourth (S4) HS components detected from the sensed HS signal.

In Example 7, the subject matter of Example 6 optionally includes the HS metric that may include a S2 intensity, and the vasoactivity monitor that is configured to determine a degree of vasodilation using an increase in S2 intensity.

In Example 8, the subject matter of Example 7 optionally includes the HS metric that may further include a S1 intensity, and the vasoactivity monitor configured to determine a degree of vasodilation using an increase in S1 intensity concurrent with an increase in S2 intensity.

In Example 9, the subject matter of any one or more of Examples 6-8 optionally includes the HS metric that may include a S2 intensity, and the vasoactivity monitor configured to determine a degree of vasoconstriction using a decrease in S2 intensity.

In Example 10, the subject matter of any one or more of Examples 6-9 optionally includes the HS metric that may further includes a S1 intensity, and the vasoactivity monitor configured to determine a degree of vasoconstriction using a decrease in S1 intensity concurrent with a decrease in S2 intensity.

In Example 11, the subject matter of any one or more of Examples 1-10 optionally includes the vasoactivity monitor configured to detect a vasovagal surge using the monitored vasoactivity.

In Example 12, the subject matter of Example 11 optionally includes a target event detector configured to detect a syncope or a pre-syncope using the detected vasovagal surge.

In Example 13, the subject matter of any one or more of Examples 1-12 optionally includes the vasoactivity monitor configured to detect a sympathetic surge using the monitored vasoactivity.

In Example 14, the subject matter of Example 13 optionally includes a target event detector configured to detect a pulmonary edema event using the detected sympathetic surge.

In Example 15, the subject matter of Example 13 optionally includes a target event detector configured to detect a worsening heart failure (WHF) event using the detected sympathetic surge.

Example 16 is a method for monitoring vasoactivity in a patient. The method comprises steps of: receiving a heart sounds (HS) signal sensed from the patient; generating a HS metric using the received HS signal; monitoring vasoactivity using the generated HS metric; and determinizing a degree of vasodilation or a degree of vasoconstriction.

In Example 17, the subject matter of Example 16 optionally includes monitoring the vasoactivity in response to a vasodilator or vasoconstrictor therapy, and the method comprises generating a therapy efficacy indicator using the monitored vasoactivity.

In Example 18, the subject matter of any one or more of Examples 16-17 optionally includes initiating or adjusting a vasoactive therapy according to the monitored vasoactivity.

In Example 19, the subject matter of any one or more of Examples 16-18 optionally includes the HS metric that may include a S2 intensity, and monitoring the vasoactivity may include detecting a degree of vasodilation using an increase in S2 intensity, or detecting a degree of vasoconstriction using a decrease in S2 intensity.

In Example 20, the subject matter of Example 19 optionally includes the HS metric that may further include a S1 intensity, and monitoring vasoactivity may include determining a degree of vasodilation using an increase in S1 intensity concurrent with an increase in S2 intensity, or determining a degree of vasoconstriction using a decrease in S1 intensity concurrent with a decrease in S2 intensity.

In Example 21, the subject matter of any one or more of Examples 16-20 optionally includes detecting a vasovagal surge or a sympathetic surge using the monitored vasoactivity.

In Example 22, the subject matter of Example 21 optionally includes detecting a target physiologic event using the detected vasovagal surge or the detected sympathetic surge.

The systems, devices, and methods discussed in this document may improve the technology of ambulatory vasoactivity monitoring, such as in assessing hemodynamic response to vasodilator therapy in HF. Conventional vasoactivity monitoring may require invasive procedure, or complicated sensing equipment. These conventional monitors and methods may also face challenges of lack of specificity or sensitivity. The present document provides a technological improvement in ambulatory vasoactivity monitoring using patient heart sounds (HS) information. The HS-based monitor may not only ensure timely attention and medical intervention in HF patient (such as by titrating vasodilator dosage), but may also avoid or reduce unnecessary medical interventions (e.g., drugs, additional procedures, or device therapies) scheduled, prescribed, or provided to those patients who are identified to have improved hemodynamics. As such, the devices and methods discussed herein would not only better align the medical resources to serve the need of more patients, but may also achieve overall system cost savings for chronically monitoring HF patients.

The systems, devices, and methods discussed in this document may also improve functionality of a medical device or a patient management system. Among other things, the present document described a HS-based vasoactivity monitoring system. The hemodynamic sensing and information processing may put a high demand for battery power, storage space, computing and process power, and communication bandwidth. The HS-based hemodynamic monitor may reduce active operation time of the corresponding device components, and provide a power- and resource-conservative solution to ambulatory vasoactivity monitoring with improved efficiency at lower operation cost. Additionally, as HS sensors have been used for ambulatory cardiac monitoring, the HS-based vasoactivity monitoring as discussed herein requires little extra hardware beyond what an ambulatory cardiac monitor may generally provide.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 3A-3B are graphs illustrating examples of a change in HS metrics following vasodilator intake in a group of patients.

DETAILED DESCRIPTION

Disclosed herein are systems, devices, and methods for monitoring patient vasoactivity. An exemplary patient monitor system can monitor vasoactivity, such as degree of vasoconstriction or vasodilation, using heart sounds (HS) metrics generated from patient HS signal. The system can provide the monitored vasoactivity to a user to alert patient hemodynamic responses to vasoactive drugs, generate or adjust a vasoactive therapy according to the monitored vasoactivity, or to detect a medical condition, such as worsening heart failure, pulmonary edema, or syncope.

Figure 1:
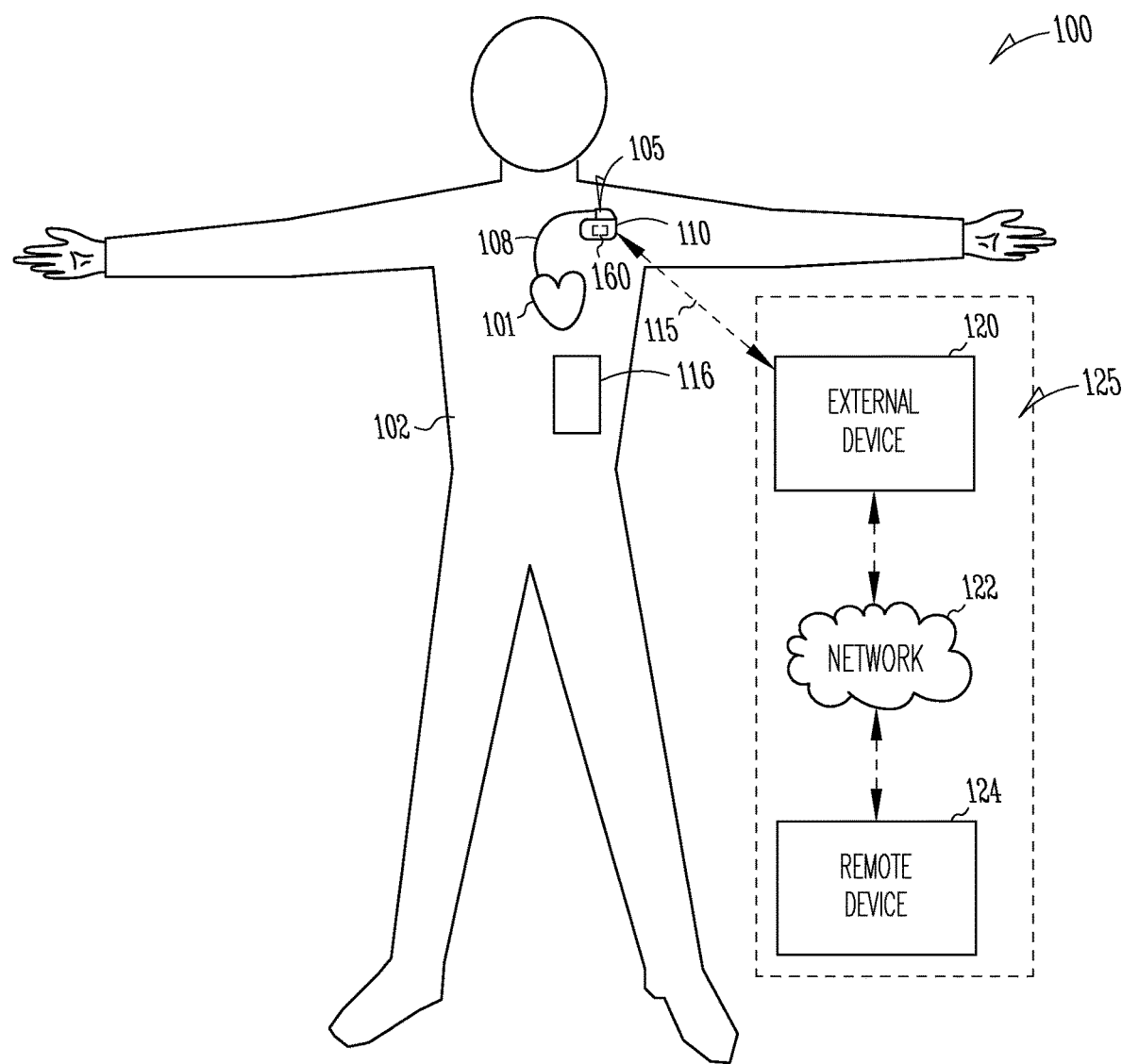
FIG. 1 illustrates generally an example of a patient monitor system and portions of an environment in which the system may operate. [0036]1

FIG. 1 illustrates generally an example of a patient monitor system 100 and portions of an environment in which the system 100 may operate. The patient monitor system 100 may chronically monitor a patient 102 to detect and evaluate a syncopal event. Portions of the system 100 may be ambulatory. Portions of the system 100 may be disposed in the patient's home or office, a hospital, clinic, or physician's office. The patient monitor system 100 may include an ambulatory system 105 associated with the patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. The physiologic signals may contain information about patient physiologic response to a precipitating event associated with onset of a future syncopal event. The physiologic signal may represent changes in patient hemodynamic status. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a vasoactivity monitor 160 for monitoring patient vasoactivity, such as vasodilation or vasoconstriction, using one or more physiologic signals. In an example, the vasoactivity monitor 160 may detect patient hemodynamic responses to vasoactivity. The monitored vasoactivity may represent vasodilation or vasoconstriction due to changes in pathophysiology such as progression of a heart disease, or produced by electrostimulation or drug therapy. The hemodynamic response may be sensed using various physiologic sensors, including pressure sensors, impedance sensors, temperature sensor, heart sound (HS) sensors, pulse oximeters, among others. Hemodynamic data acquisition may be initiated in response to a precipitating event, such as a change in heart rate, medication intake (e.g., vasodilators for HF patients), a patient trigger (e.g., development of a symptom or condition), a medical event (e.g., hospitalization or clinic visit, a change of medication type or dose), or a time of a day. In an example, the vasoactivity monitor 160 may generate an indicator of hemodynamic profile using HS metrics generated from a HS signal sensed from the patient. The vasoactivity monitor 160 may monitor vasoactivity based on the hemodynamic profile indicator. In some examples, the AMD 110 may further detect a medical condition, such as WHF, pulmonary edema, or syncope, using the monitored vasoactivity. Examples of the vasoactivity detection are discussed below, such as with reference to FIGS. 2-4.

The AMD 110 may include a therapy circuit configured to generate and deliver a therapy to the patient, such as in response to the monitored vasoactivity or the detected medical condition. The therapy may be preventive or therapeutic in nature such as to modify, restore, or improve patient cardiac, respiratory, or neural functions. Examples of the therapy may include electrical, magnetic, or other forms of therapy. In some examples, the patient monitor system 100 may include a drug delivery system 116, such as a drug infusion pump, to deliver medication, such as diuretics or vasodilators for treating or alleviating symptoms of HF. The drug delivery system 116 may be computerized and in communication with the vasoactivity monitor 160. The AMD 110 may trend vasoactivity measurements over time, and use said trend to assess progression of a medical condition (e.g., WHF), predict a risk of a future medical event (e.g., HF decompensation or a syncope episode), assess a therapeutic effect of a therapy (e.g., a device therapy provided by the AMD 110, or a drug therapy provided by the drug delivery system 116), or modify a therapy if needed.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to monitor vasoactivity, or optionally delivering or adjusting a therapy via the AMD 110 or the drug delivery system 116. The external system 125 may communicate with the AMD 110 via the communication link 115. The device data received by the external system 125 may include real-time or stored physiologic data from the patient 102, diagnostic data such as detected degree of vasodilation or vasoconstriction, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi-, or distributed computing and processing system. In an example, the remote device 124 may include a data processor configured to perform further data analysis, such as detection of degrees of vasodilation or vasoconstriction, using the signals received by the AMD 110. Computationally intensive algorithms, such as machine-learning algorithms, may be implemented in the remote device 124 to process the data retrospectively to confirm, reject, or modify the vasoactivity detection provided by the AMD 110. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the information about the vasoactivity to a system user such as the patient or a clinician. The clinician may review, perform further analysis, or adjudicate the device detection. The monitored vasoactivity, optionally along with the physiologic and hemodynamic data, may be output to a process including an instance of a computer program executable in a microprocessor. In an example, the process may include an automated generation of recommendations for initiating or adjusting a therapy, or a recommendation for further diagnostic test or treatment. In an example, the external device 120 or the remote device 124 may include a respective display unit for displaying the physiologic and hemodynamic signals, or alerts, alarms, emergency calls, or other forms of warnings about the detection of vasoactivity and/or other detected medical conditions.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
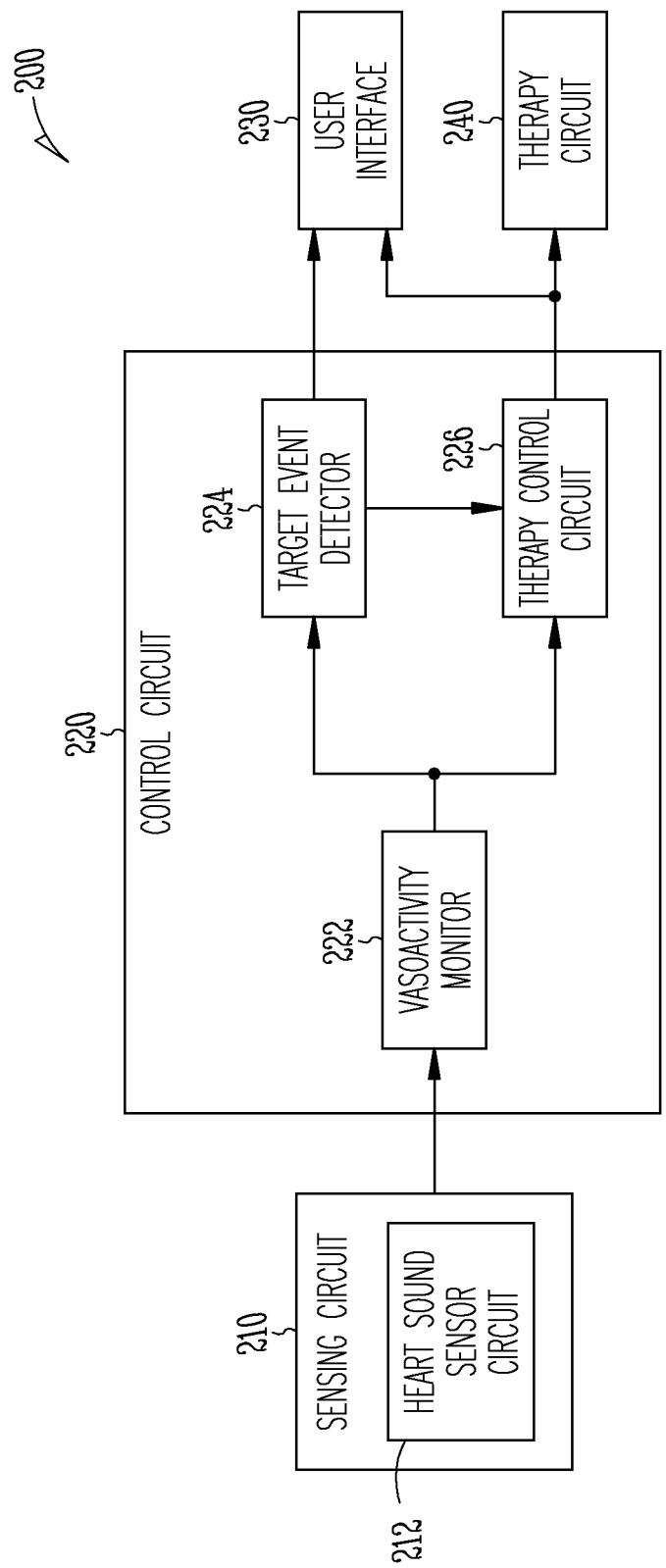
FIG. 2 illustrates generally an example of a vasoactivity monitor system configured to monitor vasoactivity in a patient.

FIG. 2 illustrates generally an example of a vasoactivity monitor system 200 configured to monitor vasoactivity in a patient. At least a portion of the vasoactivity monitor system 200 may be implemented in the AMD 110, the external system 125 such as one or more of the external device 120 or the remote device 124, or distributed between the AMD 110 and the external system 125.

As illustrated in FIG. 2, the vasoactivity monitor system 200 may include one or more of a sensing circuit 210, a process detector 220, and a user interface 230. The vasoactivity monitor system 200 may include an optional therapy circuit 240 for delivering a therapy to treat medical conditions associated with the monitored vasoactivity.

The sensing circuit 210 may sense a physiologic signal from the patient. In an example, the sensing circuit 210 may include a sense amplifier circuit to sense the physiologic signal from a patient via a physiologic sensor, such as an implantable, wearable, or otherwise ambulatory sensor or electrodes associated with the patient. The sensor may be incorporated into, or otherwise associated with an ambulatory device such as the AMD 110. In some examples, the physiologic signals sensed from a patient may be stored in a storage device, such as an electronic medical record (EMR) system. The sensing circuit 210 may receive the physiologic signal from the storage device, such as in response to a user command or a triggering event. Examples of the physiologic signals for detecting the precipitating event may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensing circuit 210 may include one or more sub-circuits to digitize, filter, or perform other signal conditioning operations on the received physiologic signal.

In an example, the sensing circuit 210 may include a heart sound (HS) sensor circuit 212 configured to generate one or more HS metrics using HS information of the patient. The sensing circuit 210 may be communicatively coupled to a heart sound sensor to sense a HS signal. The HS sensor may take the form of an accelerometer, an acoustic sensor, a microphone, a piezo-based sensor, or other vibrational or acoustic sensors. The accelerometer can be a one-axis, two-axis, or a three-axis accelerometer. Examples of the accelerometer may include flexible piezoelectric crystal (e.g., quartz) accelerometer or capacitive accelerometer, fabricated using micro electro-mechanical systems (MEMS) technology. The HS sensor may be included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various HS components.

The HS sensor circuit 212 may filter the sensed HS signal through a filter. In an example, the filter may be band-pass filter having a pass-band frequency of approximately between 5 and 90 Hz, or approximately between 9 and 90 Hz. In an example, the filter may include a double or higher-order differentiator configured to calculate a double or higher-order differentiation of the heart sound signal. The HS analyzer circuit may compute an ensemble average of the HS signal over multiple cardiac cycles, or over a specified time period. One or more HS components may be detected from the HS signal, including a first (S1) heart sound, a second (S2) heart sound, a third (S3) heart sound, or a fourth (S4) heart sound using respective time windows. S1 is associated with the vibrational sound made by the heart during tensing of the mitral valve. S2 is produced by the closure of the aortic and pulmonary valves, and marks the beginning of diastole. S3 is an early diastolic sound corresponding to passive ventricular filling during diastole, when the blood rushes into the ventricles. S4 is a late diastolic sound corresponding to active ventricular filling when the atria contract and push the blood into the ventricles.

The HS sensor circuit 212 may generate one or more HS metrics using the detected HS components. Examples of the HS metrics may include an intensity (e.g., amplitude or signal energy under the curve) of a HS component, or one or more HS-based cardiac timing intervals, such as a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. These HS-based cardiac timing intervals may be correlated with cardiac contractility or cardiac diastolic function of the heart. The HS metrics may further include PEP/LVET ratio, STI/DTI ratio, STI/cycle length (CL) ratio, or DTI/CL ratio, or other composite metrics.

The control circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The control circuit 220 may include circuit sets comprising one or more other circuits or sub-circuits, such as a vasoactivity monitor 222, a target event detector 224, and a therapy control circuit 226. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The vasoactivity monitor 222 may monitor vasoactivity from a patient, such as vasoconstriction or vasodilation due to pathophysiology of a medical condition, or produced by electrostimulation or drug therapy. In an example, the vasoactivity may be detected using one or more HS metrics produced by the HS sensor circuit 212. Various HS metrics have been found to be correlated to cardiac hemodynamics. For example, S1 intensity (e.g., amplitude of signal energy) is correlated to LV contractility. S2 intensity is correlated to pressure gradient across the aortic valve ($P_{AG}$) at the time of aortic valve closure, that is, $P_{AG}$=AoP−LVEDP, where AoP denotes aortic pressure and LVEDP denotes left-ventricular end-diastolic pressure. As discussed above, patients in HF generally have a flattened Frank-Starling curve, such that more venous return and filling pressure is required to maintain contractility and stroke volume. A vasodilation therapy (e.g., through vasodilator drug or electrostimulation therapy) may generally cause a drop in blood pressure, and thus a drop in AoP (that is, AoP<$AoP_0$, where $AoP_0$ denotes pre-dilation aortic pressure, and AoP denotes post-dilation aortic pressure). The vasodilation may also shift the Frank-Starling curve upward and leftward, resulting in an increase in cardiac contractility (or stroke volume) and a decrease in LVEDP (that is, LVEDP<$LVEDP_0$, where $LVEDP_0$ denotes pre-dilation LV end-diastolic pressure, and LVEDP denotes post-dilation LV end-diastolic pressure). Such hemodynamic effects may be reflected in changes in HS metrics. For example, the improved contractility may be reflected in an increase in S1 intensity. The decrease in LVEDP, when exceeding the amount of drop in AoP (that is, when $LVEDP_0$−LVEDP>$AoP_0$−AoP), would result in an increase in the pressure gradient across the aortic valve $P_{AG}$, that is, $P_{AG}$=AoP−LVEDP>$P_{AG0}$=$AoP_0$−$LVEDP_0$. As such, an increase in S2 intensity is expected following a vasodilation therapy.

The pressure gradient across the aortic valve ($P_{AG}$), and thus the S2 intensity, reflect a balance between a hemodynamically favorable effect of reduced LVEDP and an unfavorable effect of drop in blood pressure or AoP. In an example, the vasoactivity monitor 222 may monitor and quantify vasodilation using S2 intensity. If S2 intensity increases over a baseline S2 intensity (e.g., prior to a vasodilator therapy), an increase in $P_{AG}$ is indicated, suggesting a substantially greater reduction in LVEPD for a given drop in blood pressure. The vasoactivity monitor 222 may generate a vasoactivity indicator indicating whether adequate vasodilation has occurred. If S2 intensity decrease from a baseline S2 intensity, a decrease in $P_{AG}$ is indicated, suggesting insufficient reduction in LVEDP to counter the blood pressure drop. Accordingly, the vasoactivity monitor 222 may generate a vasoactivity indicator indicating inadequate vasodilation. In some examples, the vasoactivity indicator may be represented as a numerical value proportional to a relative difference between the measured S2 intensity and the baseline S2 intensity.

In some examples, the vasoactivity monitor 222 may monitor and quantify vasodilation using both the S2 intensity and S1 intensity. An increase in S1 intensity may indicate an effective decrease in LVEDP, and an increase in S2 intensity may indicates that the decrease in LVEDP is more substantial than the blood pressure drop induced by vasodilation. An adequate vasodilation effect is indicated if both the increase in S1 intensity and the increase in S2 intensity satisfy respective conditions such as exceeding respective thresholds. A combination of S1 and S2 may yield more accurate characterization and quantification of the vasoactivity with fewer false positive detections. In some examples, S1 intensity may be used to confirm a vasoactivity based on S2 intensity. For example, the S1 intensity may be checked against its baseline level only when S2 intensity is determined to increase over the baseline S2 intensity.

The vasoactivity monitor 222 may additionally or alternatively monitor vasoconstriction using the HS metrics. Vasoconstriction may increase blood pressure, and cause the Frank-Starling curve to shift in opposite directions than vasodilation. The vasoactivity monitor 222 may monitor vasoconstriction using a decrease in S2, alone or in combination with a decrease in S1.

Although the discussed above with respect to vasoactivity monitoring pertains to response to drug or electrical therapies that produce vasoconstriction or vasodilation effects, this is only meant by way of example but not limitation. The vasoactivity monitor 222 may also be configured to monitor vasoconstriction or vasodilation in certain pathophysiologic events. The target event detector 224 may be configured to detect a target physiologic event using the monitored vasoactivity. Certain cardiovascular or neurological conditions may cause acute or chronic vasoconstriction or vasodilation effects. Examples of detecting medical conditions using the HS-based vasoactivity are discussed in the following, such as with reference to FIGS. 4A-4C.

The therapy control circuit 226 is configured to assess an efficacy of a vasoactivity modulation therapy, and adjust said therapy, based on the vasoactivity indicator produced by the vasoactivity monitor 222. As discussed above, the vasoconstriction or vasodilation may be caused by vasoactivity modulation therapy, such as a medical therapy (e.g., vasodilator drugs) or a device therapy (e.g., electrostimulation or cardiac, neural, or other tissue). The therapy control circuit 226 may generate a therapy titration protocol based on the vasoactivity indicator, and optionally further based on the detected target event provided by the target event detector 224. The therapy titration protocol may include an up-titration and/or a down-titration of drug dosage, timing, and duration; or one or more electrostimulation parameter such as stimulation site, stimulation vector configuration (e.g., anode and cathode electrodes), stimulation strength (e.g., pulse amplitude, pulse width, pulse frequency, pulse waveform, duty cycle, or pacing duration, among other parameters), stimulation timing or duration.

In an example of monitoring effect of vasodilator therapy in a HF patient, if the vasoactivity indicator indicates an inadequate vasodilation effect, the therapy may be up-titrated, such as an increase in quantity or frequency of medication dose at specified time or manner, an increase in electrostimulation intensity or duration at specified time or manner, or addition of a new medication or device therapy such as to boost therapeutic effect at specified time or manner. Conversely, if the vasoactivity indicator indicates an adequate vasodilation effect, the therapy may be down-titrated, such as a decrease in quantity or frequency of medication dose at specified time or manner, a decrease in electrostimulation intensity or duration at specified time or manner, or cutback of a present medication or device therapy at specified time or manner. In some examples, up- or down-titration of therapy may be triggered by one or more medical events. For example, a down-titration of vasodilator and/or diuretic may be initiated if the patient is over diuresis, or an up-titration of vasodilator and/or diuretic may be initiated if the patient undergoes a surgery that requires intravenous fluid infusion.

The user interface 230 may include an input unit and an output unit. In an example, at least a portion of the user interface 230 may be implemented in the external system 125. The input unit may receive user input for programming the sensing circuit 210 and the control circuit 220, such as parameters for detecting HS components and generating HS metrics, monitoring vasoactivity using S1 intensity and/or S2 intensity, and parameters for detecting the target physiologic event. The input unit may include a keyboard, on-screen keyboard, mouse, trackball, touchpad, touch-screen, or other pointing or navigating devices. The output unit may include a display for displaying the patient physiologic data (e.g., HS data and HS metrics), the vasoactivity indicator, the detected target events, and any intermediate measurements or computations, among others. The output unit may also present to a user, such as via a display unit, the therapy titration protocol and recommended therapy, including a change of parameters in the therapy provided by an implanted device, the prescription to get a device implanted, the initiation or change in a drug therapy, or other treatment options of a patient. The output unit may include a printer for printing hard copies of signals and the vasoactivity indicator and the detected physiologic event. The signals and information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events.

The therapy circuit 240 may be configured to deliver a therapy to the patient, such as in response to the detected physiologic event, or when the vasoactivity indicator satisfies a specific condition (e.g., insufficient vasodilation or vasoconstriction). The therapy may be delivered in accordance with the therapy titration protocol provided by the therapy control circuit 226. The therapy may be preventive or therapeutic in nature such as to modify, restore, or improve patient neural, cardiac, or respiratory functions. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 240 may modify an existing therapy, such as adjust a stimulation parameter or drug dosage.

FIGS. 3A-3B are graphs illustrating examples of changes in HS metrics following vasodilator intake in a group of patients. By way of example and not limitation, two HS metrics, S1 amplitude and S2 amplitude, were measured before and after vasodilation. The HS metrics data were obtained from a number of HF patients, and statistical results (mean and standard deviation) are presented herein. FIG. 3A illustrates pre-vasodilation S1 amplitude 311 and post-vasodilation S1 amplitude 312 (both expressed and shown as mean+/−standard deviation). In this example, the post-vasodilation S1 amplitude 312 is statistically significantly higher than the pre-vasodilation S1 amplitude 311. FIG. 3B illustrates pre-vasodilation S2 amplitude 321 and post-vasodilation S2 amplitude 322 (both expressed and shown as mean+/−standard deviation). The post-vasodilation S2 amplitude 322 is statistically significantly higher than the pre-vasodilation S2 amplitude 321. The illustrated data and results demonstrate that HS metrics such as S1 and S2 intensities are useful and effective hemodynamic indicators indicating vasodilation response in patients. As HS sensors and processing are relatively low cost, and the HS signal can be acquired non-invasively, the HS-based vasodilation assessment as discussed herein is advantageous over the conventional apparatus and methods of hemodynamic monitoring particularly for patients in an ambulatory setting.

Figure 4A:
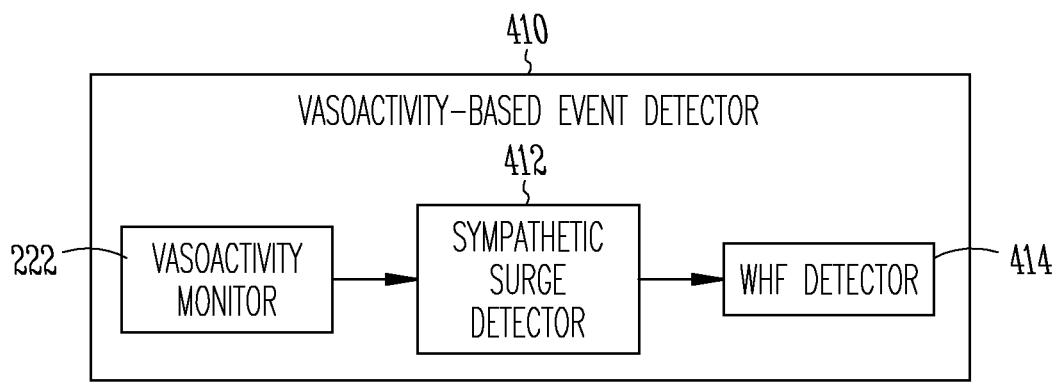
FIGS. 4A-C illustrate generally examples of vasoactivity-based event detector configured to detect various physiologic events based on the monitored vasoactivity.
Figure 4B:
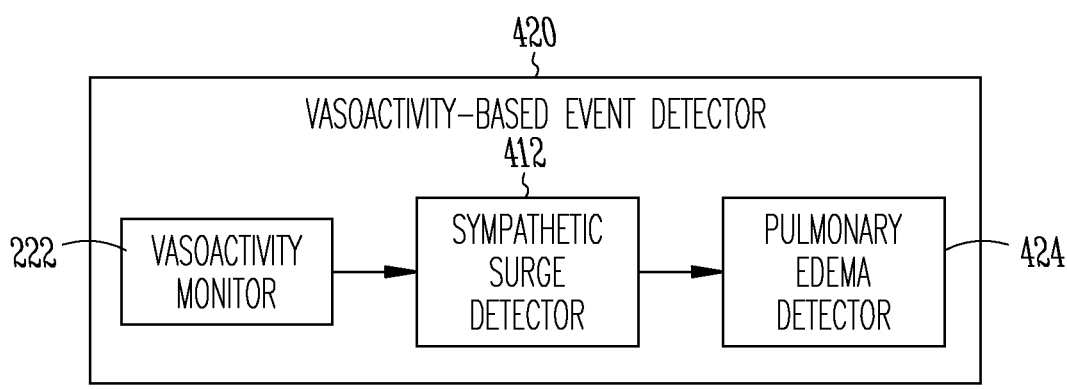
Figure 4C:
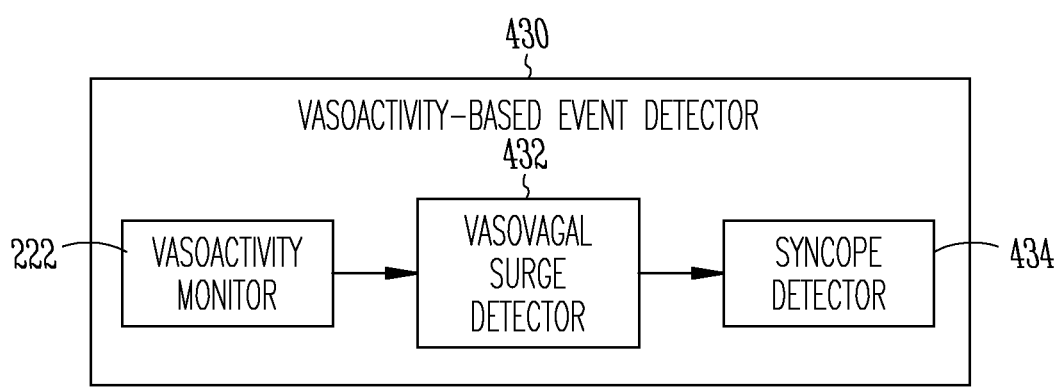

FIGS. 4A-C illustrate generally examples of vasoactivity-based event detectors 410, 420, and 430 configured to detect various physiologic events using vasoactivity detected by the vasoactivity monitor 222. The vasoactivity-based event detectors 410, 420, and 430 are embodiments of the control circuit 220 as illustrated in FIG. 2. As illustrated in FIGS. 4A-4B, the vasoactivity-based event detectors 410 and 420 each includes a sympathetic surge detector 412 configured to detect sympathetic surge based on the monitored vasoactivity. A vasoconstriction effect may be indicative of sympathetic surge. The vasoactivity monitor 222 may detect a vasoconstriction effect using one or more HS metric, such as a decrease in S2 intensity from a corresponding baseline value, or additionally accompanied by a decrease in S1 intensity from a corresponding baseline value. The sympathetic surge detector 412 may detect the sympathetic surge based on vasoconstriction effect.

The detected sympathetic surge may be reported or presented to a user such as via the user interface 230. Additionally or alternatively, information about the sympathetic surge may be used to detect a medical condition. FIG. 4A illustrates a WHF detector 414 configured to detect a WHF event based on the detected sympathetic surge. Progressive worsening of HF may result in flattening of Frank-Starling curve, characterized by increases in LVEDP and decrease in contractility and stroke volume. This is analogous to vasoconstriction effect. Hyperactivity of sympathetic nervous system may contribute to the development of left ventricular diastolic dysfunction and account for the increased cardiovascular risk. The sympathetic hyperactivity observed in HF patients is closely related to abnormalities in cardiovascular reflexes. The chronic increase in sympathetic output is associated with structural and functional changes in the cardiomyocytes, and can lead to left ventricular dilation and systolic dysfunction (LV remodeling). In some examples, the WHF detector 414 may additionally use information from other physiologic sensors, such as thoracic impedance, respiration, activity, heart rate and heart rate variability, etc. FIG. 4B illustrates a pulmonary edema detector 424 configured to detect pulmonary edema based on the detected sympathetic surge. Sympathetic surge and increased peripheral vascular resistance may lead to acute pulmonary edema. Patient can be presented with markedly elevated blood pressure, severe dyspnea, and desaturation. In some examples, the pulmonary edema detector 424 may additionally use information from other physiologic sensors, such as thoracic impedance, blood pressure sensor, and respiration sensor to detect or confirm pulmonary edema. In an example, these additional sensors (e.g., thoracic impedance and BP) may be used in response to concurrent decrease in both S1 intensity and S2 intensity.

FIG. 4C illustrates a processor circuit 430 that includes vasovagal surge detector 432 configured to monitor vasovagal surge based on the monitored vasoactivity. A vasodilation effect may be indicative of vasovagal surge. The vasoactivity monitor 222 may detect a vasodilation effect using one or more HS metric, such as an increase in S2 intensity from a corresponding baseline value, or additionally accompanied by an increase in S1 intensity from a corresponding baseline value, as discussed above in reference to FIG. 2. The vasovagal surge detector 432 may monitor vasovagal surge based on vasodilation effect.

The detected vasovagal surge may be reported or presented to a user such as via the user interface 230. Additionally or alternatively, information about the vasovagal surge may be used to detect syncope or pre-syncope via a syncope detector 434, as illustrated in FIG. 4C. Syncope is characterized by an abrupt loss of consciousness with a concomitant loss of postural tone. Decreased cerebral perfusion is common to all causes of syncope. One type of syncope is cardiogenic syncope, often caused by irregular heart rhythms. Patients with underlying cardiac disease, such as arrhythmias or structural cardiopulmonary diseases, are at higher risk of cardiogenic syncope. Majority of syncope are non-cardiac in nature, including neurally mediated syncope (or vasovagal syncope, VVS), and orthostatic syncope (or orthostatic hypotension, OH). The VVS is a disorder of the autonomic regulation of postural tone, and may be related to vasovagal, carotid sinus, or situational causes of hypotension. Patients with VVS may present with marked slowing of heart rate and/or inappropriate vasodilation. In an example, the syncope detector 434 may additionally use information from other physiologic sensors, such as heart rate, blood pressure, and respiration to detect or confirm syncope. In some examples, the detected vasovagal surge may be used to differentiate VVS from other types of syncope, such as cardiogenic syncope or orthostatic syncope, as the vasovagal surge is more likely to occur during the VVS, causing a sudden drop in blood pressure and heart rate such as during heal-up tilt, than cardiogenic or orthostatic syncope.

Figure 5:
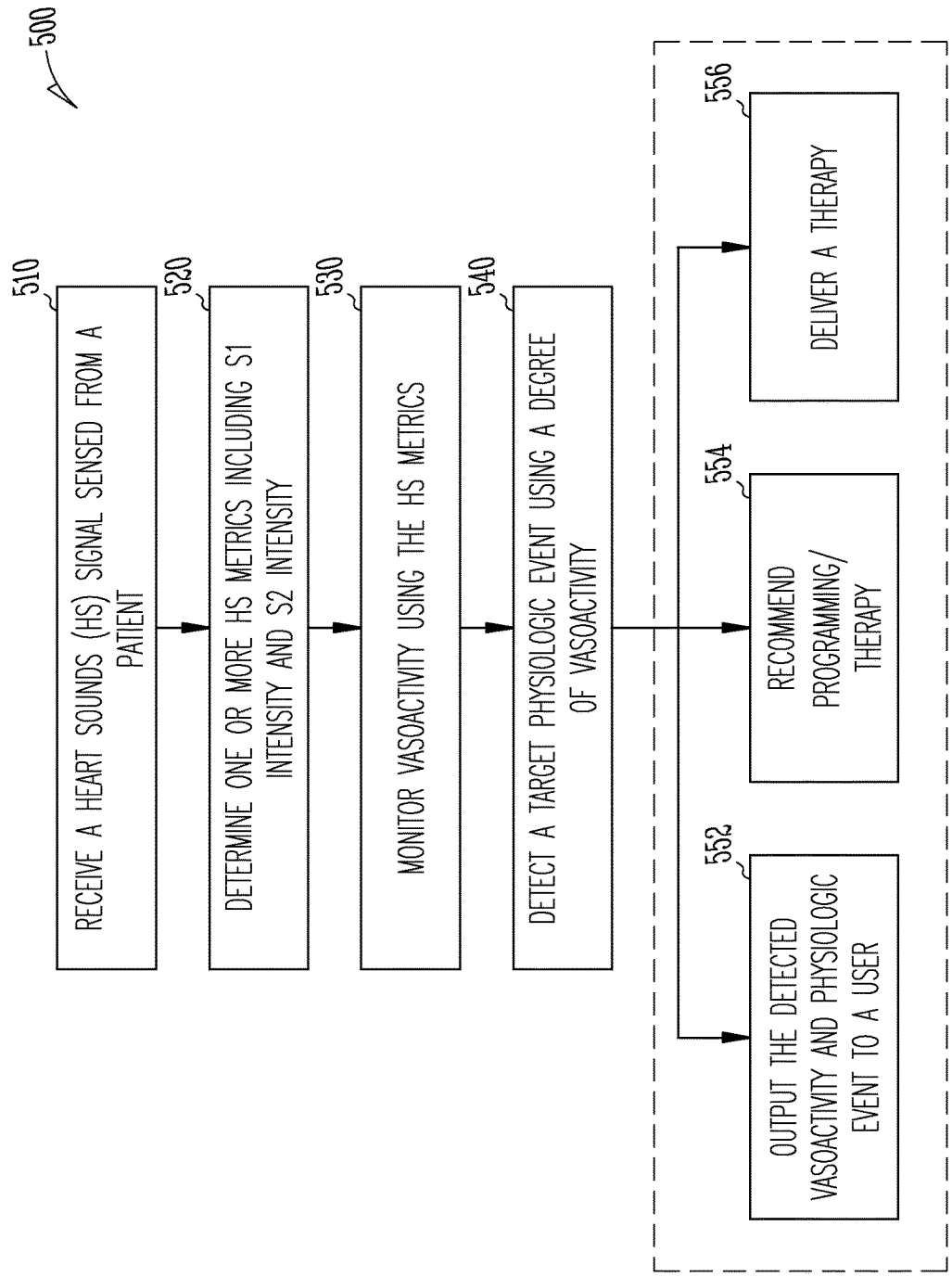
FIG. 5 illustrates generally an example of a method for monitoring vasoactivity in a patient.

FIG. 5 illustrates generally an example of a method 500 for monitoring vasoactivity in a patient. In an example, the method 500 may be implemented in and executed by the cardiac arrhythmia detection circuit 160 in the AMD 110, the external system 130, or the vasoactivity monitor system 200.

The method 500 commences at step 510, where one or more physiologic signals including a heart sounds (HS) signal may be received. The HS signal may be sensed using a HS sensor, such as an accelerometer, an acoustic sensor, a microphone, a piezo-based sensor, or other vibrational or acoustic sensors that are included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. Other physiologic signal may also be received, which may include surface ECG, subcutaneous ECG, intracardiac EGM, heart rate signal, physical activity signal, or posture signal, a thoracic or cardiac impedance signal, blood pressure signal, blood oxygen saturation signal, physiologic response to activity, apnea hypopnea index, one or more respiration signals such as a respiration rate signal or a tidal volume signal, brain natriuretic peptide (BNP), blood chemical levels, etc.

At 520, one or more HS metrics may be generated using the sensed HS signal. One or more HS components may be detected from the HS signal, including a first (S1) heart sound, a second (S2) heart sound, a third (S3) heart sound, or a fourth (S4) heart sound using respective time windows. HS metrics may be generated using the detected HS components. By way of example and not limitation, the HS metrics may include an intensity (e.g., amplitude or signal energy under the curve) of a HS component, one or more HS-based cardiac timing intervals such as PEP, STI, LVET, DTI, as discussed above with reference to FIG. 2, or composite HS metrics.

At 530, vasoactivity may be detected using at least the HS metrics, such as by using the vasoactivity monitor 222. The vasoactivity may include vasoconstriction or vasodilation due to pathophysiology of a medical condition, or produced by electrostimulation or drug therapy. In an example, a vasoactivity indicator may be generated using S2 intensity. S2 intensity is correlated to pressure gradient across the aortic valve at the time of aortic valve closure. In an example, the vasoactivity indicator may be represented as a numerical value proportional to a relative difference between the measured S2 intensity and the baseline S2 intensity. An increase in S2 intensity over a baseline S2 intensity (e.g., prior to a vasodilator therapy) indicates an increase in the pressure gradient across the aortic valve, suggesting a substantially greater reduction in LVEPD for a given drop in blood pressure. Such a vasoactivity indicator indicates adequate vasodilation. Conversely, a decrease in S2 intensity from the baseline S2 intensity may indicate insufficient reduction in LVEDP to counter the blood pressure drop, and therefore an inadequate vasodilation.

In some examples, both S2 intensity and S1 intensity may be used to quantify the vasoactivity, such as to monitor vasodilation. S1 intensity (e.g., amplitude of signal energy) is correlated to LV contractility. An increase in S1 intensity may indicate an effective decrease in LVEDP, and an increase in S2 intensity may indicates that the decrease in LVEDP is more substantial than the blood pressure drop induced by vasodilation. A combination of S1 and S2 may yield more accurate characterization and quantification of the vasoactivity with fewer false positive detections.

The vasoactivity monitor 222 may additionally or alternatively detect vasoconstriction using the HS metrics. Vasoconstriction may increase blood pressure, and cause the Frank-Starling curve to shift in opposite directions than vasodilation. The vasoactivity monitor 222 may monitor vasoconstriction using a decrease in S2, alone or in combination with a decrease in S1. In various examples, HS metrics such as S1 intensity and/or S2 intensity may be used to monitor vasoconstriction. Vasoconstriction may increase blood pressure, and cause the Frank-Starling curve to shift in opposite directions than vasodilation. A decrease in S2, alone or in combination with a decrease in S1 intensity, when satisfying specific conditions such as exceeding respective thresholds, may indicate adequate vasoconstriction effect.

At 540, a target physiologic event may be detected using the monitored vasoactivity, such as by using the target event detector 224. Certain cardiovascular or neurological conditions may cause acute or chronic vasoconstriction or vasodilation effects. In an example, a sympathetic surge may be detected based on the monitored vasoactivity. A sympathetic surge may cause vasoconstriction, and can be detected using a decrease in S2 intensity from a corresponding baseline value, or additionally accompanied by a decrease in S1 intensity from a corresponding baseline value. The sympathetic surge may be used to detect a medical condition, such as a WHF event, or a pulmonary edema event, as described above with reference to FIGS. 4A-4B. In another example, a vasovagal surge may be detected. A vasovagal surge may cause vasodilation, and can be detected using an increase in S2 intensity from a corresponding baseline value, or additionally accompanied by an increase in S1 intensity from a corresponding baseline value. The vasovagal surge may be used to detect a medical condition, such as a syncope or pre-syncope event, or to differentiate vasovagal syncope from other cardiogenic syncope or orthostatic syncope, as described above with reference to FIG. 4C.

The monitored vasoactivity, the detected vasovagal surge, the detected sympathetic surge, and/or the detected target physiologic event, may be provided to one or more of processes 552, 554, or 556. At 552, the detected vasovagal activity and the detected physiologic event, among other information, may be presented to a user, such as displayed on a display unit of the user interface 230. In some examples, a hard copy of the detection information may be generated. In various examples, alerts, alarms, emergency calls, or other forms of warnings to signal may be generated to warn the system user about the detected target event.

Additionally or alternatively, at 554, a recommendation may be generated and provided to a user. The recommendation may include one or more of further diagnostic tests to be performed, initiating a therapy to treat the detected event, changing parameters in the therapy provided by an implanted device, the prescription to get a device implanted, the initiation or change in a drug therapy, or other treatment options of a patient. In an example of monitoring vasodilator therapy in a HF patient, if the vasoactivity indicator indicates an inadequate vasodilation effect, the therapy may be up-titrated (e.g., increase drug dose or electrostimulation intensity or duration, or addition of a new drug or device therapy to boost therapeutic effect). Conversely, if the vasoactivity indicator indicates an adequate vasodilation effect, the therapy may be down-titrated (e.g., decrease drug dose or electrostimulation intensity or, or cutback of a present medication or device therapy).

At 556, a therapy may be delivered to the patient in response to the detection of the physiologic event, or in response to the vasoactivity indicator satisfying a specific condition (e.g., insufficient vasodilation or vasoconstriction). The therapy may be delivered via the therapy circuit 240 as illustrated in FIG. 2. The therapy may be delivered in accordance with the therapy titration protocol provided by the therapy control circuit 226. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 240 may modify an existing therapy, such as adjust a stimulation parameter or drug dosage.

Figure 6:
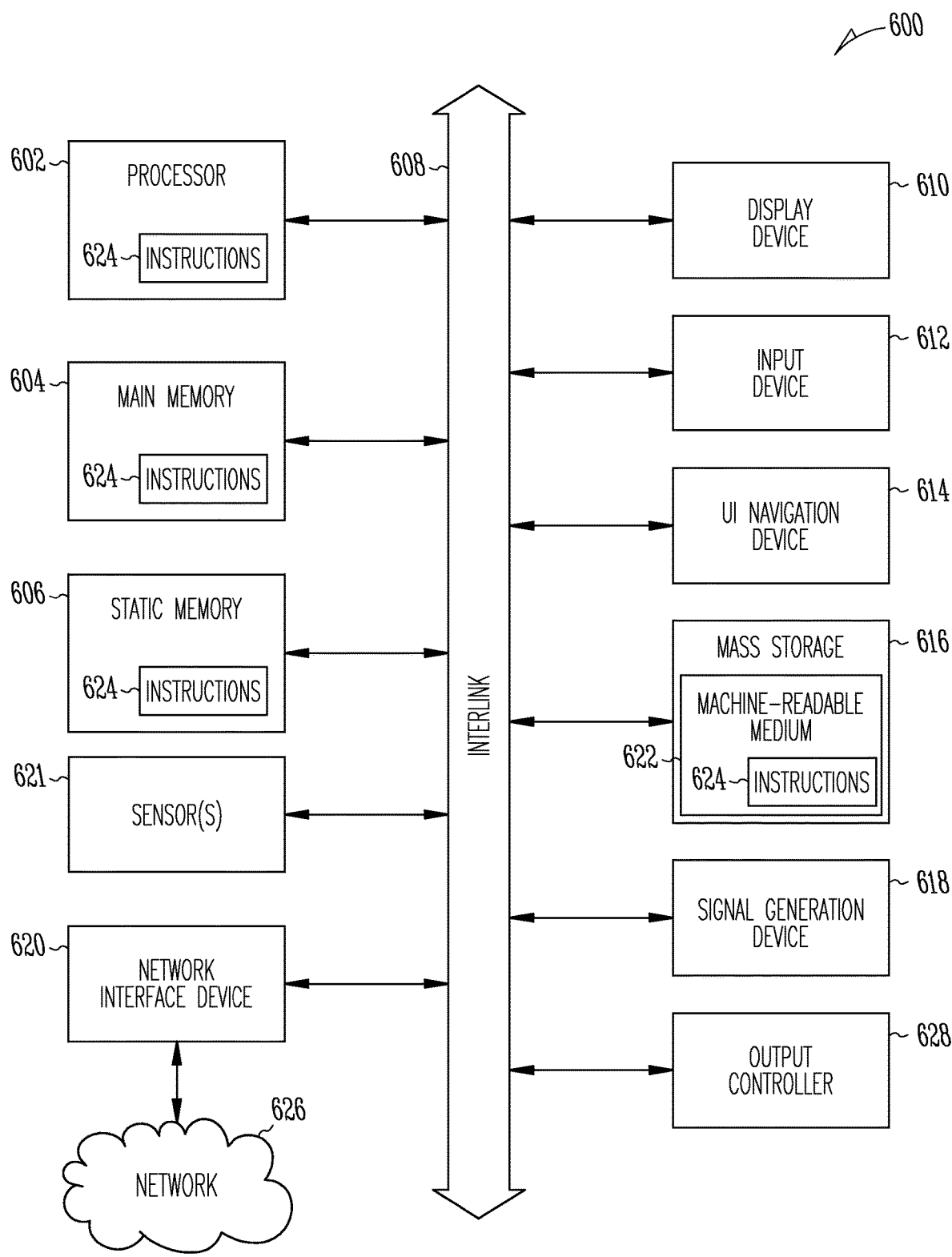
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the AMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for ambulatory monitoring of vasoactivity in a patient, comprising:
    a sensor circuit configured to generate a heart sound (HS) metric using a HS signal sensed from the patient; and
    a control circuit, including: a vasoactivity monitor configured to monitor vasoactivity and determine a degree of vasodilation using the generated HS metric; and a vasovagal surge detector configured to detect a vasovagal surge using the determined degree of vasodilation.

2. The system of claim 1, wherein the vasoactivity monitor is configured to detect the vasovagal surge in response to a vasodilator or vasoconstrictor therapy, and to generate a therapy efficacy indicator using the monitored vasoactivity.

3. The system of claim 1, comprising a therapy unit configured to generate or adjust a vasoactive therapy according to the monitored vasoactivity.

4. The system of claim 1, wherein the sensor circuit is configured to generate a HS metric using one or more HS components including first (S1), second (S2), third (S3), or fourth (S4) HS components detected from the sensed HS signal.

5. The system of claim 4, wherein the HS metric includes a S2 intensity and the vasoactivity monitor is configured to detect the vasovagal surge using an increase in S2 intensity.

6. The system of claim 5, wherein the HS metric further includes a S1 intensity, and the vasoactivity monitor is configured to detect the vasovagal surge using an increase in S1 intensity concurrent with the increase in S2 intensity.

7. The system of claim 1, comprising a target event detector configured to detect a syncope or a pre-syncope using the detected vasovagal surge.

8. A system for ambulatory monitoring of vasoactivity in a patient, the system comprising:
    a sensor circuit configured to generate a heart sound (HS) metric using a HS signal sensed from the patient; and
    a control circuit, including: a vasoactivity monitor configured to monitor vasoactivity and determine a degree of vasoconstriction using the generated HS metric; and a sympathetic surge detector configured to detect a sympathetic surge using the determined degree of vasoconstriction.

9. The system of claim 8, comprising a target event detector configured to detect a pulmonary edema event using the detected sympathetic surge.

10. The system of claim 8, comprising a target event detector configured to detect a worsening heart failure (WHF) event using the detected sympathetic surge.

11. The system of claim 8, wherein the sensor circuit is configured to generate a HS metric using one or more HS components including first (S1), second (S2), third (S3), or fourth (S4) HS components detected from the sensed HS signal.

12. The system of claim 11, wherein the HS metric includes a S2 intensity, and the vasoactivity monitor is configured to detect the sympathetic surge using a decrease in S2 intensity.

13. The system of claim 12, wherein the HS metric further includes a S1 intensity, and the vasoactivity monitor is configured to detect the sympathetic surge using a decrease in S1 intensity concurrent with the decrease in S2 intensity.

14. The system of claim 11, wherein the vasoactivity monitor is configured to detect the sympathetic surge in response to a vasodilator or vasoconstrictor therapy, and to generate a therapy efficacy indicator using the monitored vasoactivity.

15. A system for ambulatory monitoring of vasoactivity in a patient, comprising:
- a sensor circuit configured to generate a heart sound (HS) metric using a HS signal sensed from the patient;
- a control circuit, including a vasoactivity monitor configured to monitor vasoactivity and to detect a vasovagal surge using the generated HS metric; and
- a target event detector configured to detect a worsening heart failure (WHF) event based at least in part on the monitored vasoactivity.

16. The system of claim 15, wherein the sensor circuit is configured to generate a S2 intensity metric, and wherein the vasoactivity monitor is configured to detect the vasovagal surge using an increase in S2 intensity metric.

17. The system of claim 16, wherein the sensor circuit is further configured to generate a S1 intensity metric, and the vasoactivity monitor is configured to detect the vasovagal surge using an increase in S1 intensity metric concurrent with the increase in S2 intensity metric.

18. A system for ambulatory monitoring of vasoactivity in a patient, the system comprising:
- a sensor circuit configured to generate a heart sound (HS) metric using a HS signal sensed from the patient;
- a control circuit, including a vasoactivity monitor configured to monitor vasoactivity and to detect a sympathetic surge using the generated HS metric; and
- a target event detector configured to detect a worsening heart failure (WHF) event using the detected sympathetic surge.

19. The system of claim 18, wherein the sensor circuit is configured to generate a S2 intensity metric, and the vasoactivity monitor is configured to detect the sympathetic surge using a decrease in S2 intensity metric.

20. The system of claim 19, wherein the sensor circuit is further configured to generate a S1 intensity metric, and the vasoactivity monitor is configured to detect the sympathetic surge using a decrease in S1 intensity metric concurrent with the decrease in S2 intensity metric.

\* \* \* \* \*